Oct. 15, 1940. V. LENS Plant Pat. 428
ROSE PLANT
Filed June 6, 1940
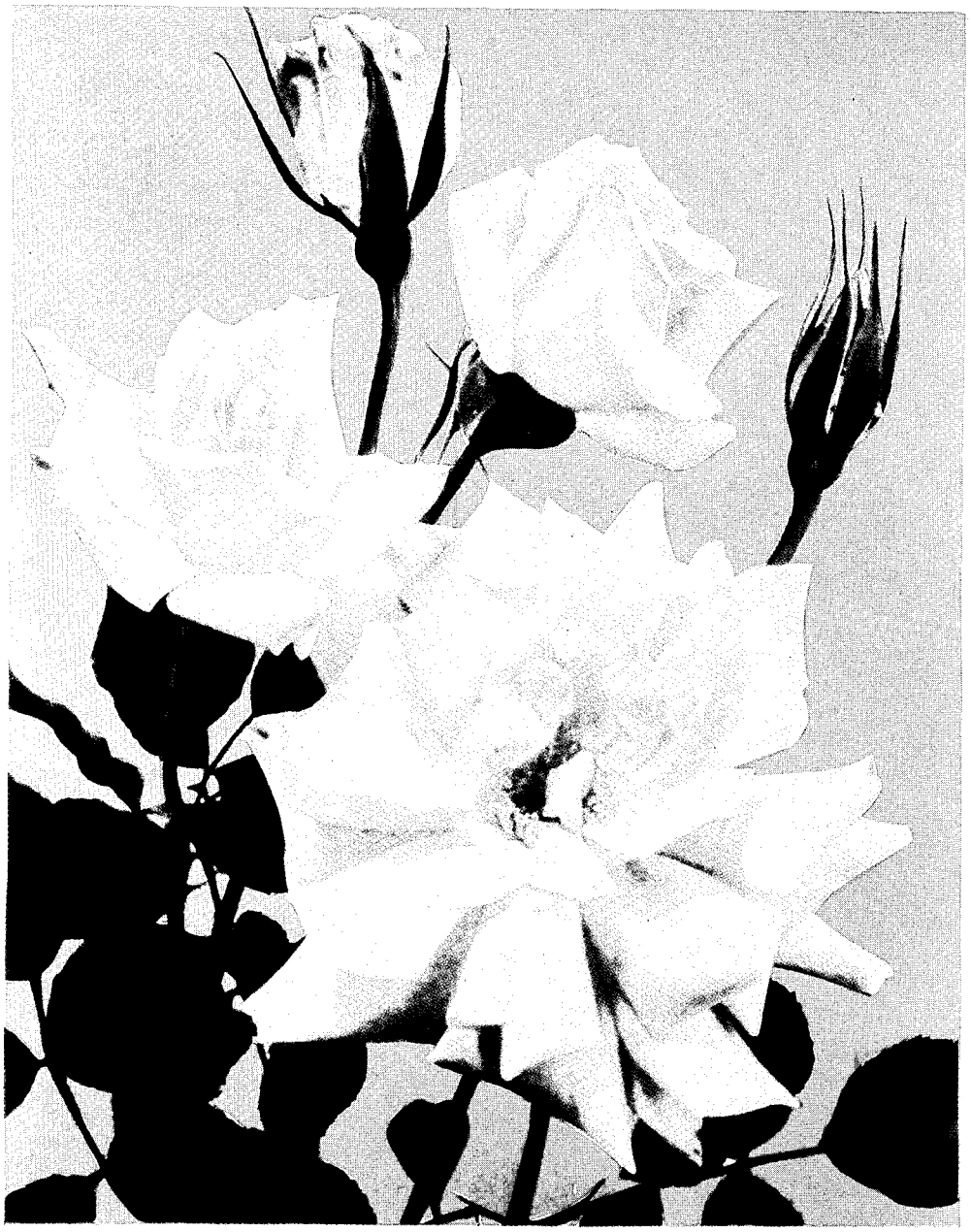
Inventor
Victor Lens
By Robbins & Robbins
Attorneys Patented Oct. 15, 1940

Plant Pat. 428

UNITED STATES PATENT OFFICE

428

ROSE PLANT

Victor Lens, Wavre Notre Dame, Belgium, assignor to Jackson & Perkins Company, Newark, N. Y.

Application June 6, 1940, Serial No. 339,191

1 Claim. (Cl. 47—61)

The present invention relates to a new and distinct variety of hybrid tea rose plant, the result of crossing the two known varieties Chas. P. Kilham and Mrs. Sam McGredy, to obtain a combination of the desirable characteristics of these varieties.

The accompanying drawing illustrates the rose in the various stages of development of the flowers, and, as nearly as possible to depict, the varying tones of coloring in these different stages.

The new variety, it will be noted, is like neither of its parents and possesses many features of distinctiveness from them as well as other varieties, among which may be importantly pointed out as novel its great floriferousness, the slender form of the buds, the high centered form of the flowers, and the varying color of the same.

Of further importance is the great number of stamens and their decorative value in the particular color combination when the flowers are open.

So far as the plant itself is concerned, the following characteristics are notable: vigorous habit of growth with long flowering stems, the large number of leaflets with brick red coloring of the upper side of the leaf stems.

Other features of distinction will be found in a more detailed description of the variety as follows, in which color terminology accords with Ridgway's Color Standard:

Parentage: Seedling.
*Seed parent.*—Chas. P. Kilham.
*Pollen parent.*—Mrs. Sam McGredy.

Classification:
*Botanic and commercial.*—Hybrid tea.

*Flower*

(Observations made at Newark, New York, in the morning of December 8, 1939.)

Blooming habit: Recurrent—continuous.

Bud:
*Size.*—Large.
*Form.*—Ovoid. Is not affected by wet or hot weather.
*Color.*—When sepals first divide—Coral Red, Plate 13. When petals begin to unfurl—between Light Coral Red, Plate 13, and Coral Red, Plate 13. When half blown: inside of petals—Flesh-Ocher, Plate 14; reverse of petals—Light Coral Red, Plate 13.
*Sepals*—Slightly branched. *Color*—Light Cress Green, Plate 31. Curl back as soon as bud starts breaking apart.
*Calyx.*—*Shape*—funnel. *Size*—broad. *Aspect*—smooth. *Color*—Cress Green, Plate 31. *Odor when rubbed*—odorless.
*Peduncle.*—*Length*—very long. *Aspect*—prickly. *Color*—Light Cress Green, Plate 31. *Strength*—erect, rather slender.
*Opening.*—Bud opens well. Is not affected by adverse conditions.

Bloom:
*Size.*—Large. Average size when fully expanded, 4½".
*Borne.*—Several together.
*Stems.*—Long; normal strength.
*Form.*—When first open—high center. *Permanence*—retains its form to the end.
*Petalage.*—Double (full but open center). Number of petals under normal conditions, 26.
*Color.*—Center of flower—Flesh Ocher, Plate 14. Outer petals—Ochraceous Buff, Plate 15. Base of petals (aiglet)—Amber Yellow, Plate 16. Inside of petals—Flesh Ocher, Plate 14, diffusing into Primuline Yellow, Plate 16, at base of petal. Reverse of petals—Ochraceous Salmon, Plate 15. General tonality from a distance—Ochraous Salmon, Plate 15.
*Discoloration.*—General tonality at end of first day: center of flower—Carrot Red, Plate 14; outer petals of flower—Ochraceous Buff, Plate 15. Second day: center of flower—Ochraceous Salmon, Plate 15; outer petals of flower—Light Ochraceous Buff, Plate 15. Third day—Salmon Buff, Plate 14.

Petals:
*Texture.*—Thick. Is not affected by wet or hot weather.
*Appearance.*—Inside shiny. Outside—satiny.
*Form.*—Oval.
*Arrangement.*—Informal (with "rags" in center). *Petaloids in center*—few, large.
*Persistence.*—Drop off cleanly.
*Fragrance.*—Moderate. *Nature*—fruity (Russet apple).
*Lasting quality.*—On the plant and as cut flower—long.

Genital organs:
*Stamens, anthers.*—Large; many. *Color*—Apricot Yellow, Plate 4. *Arrangement*—regular around styles.
*Stamens, Filaments (threads).*—Long. *Color*—Apricot Yellow, Plate 4.
*Pollen.*—Buff Yellow, Plate 4.

*Styles.*—Bunched; medium length; medium weight.

*Stigmas.*—Maize Yellow, Plate 4.

*Ovaries.*—All enclosed in calyx.

Fruit: Variety has not seeded.

*Plant*

Form: Bush.

Growth: Very vigorous with long flowering stems.

Foliage: 5 to 9 leaflets.

*Size.*—Medium.

*Quantity.*—Normal.

*Color.*—*New foliage:* upper side—Light Cress Green, Plate 31, overcast with Brick Red, Plate 13; under side—Brick Red, Plate 13, with mid-rib Light Cress Green, Plate 31. *Old foliage:* upper side—Dark Cress Green, Plate 31; under side—Light Cress Green, Plate 31.

*Shape.*—Oval pointed.

*Texture.*—Upper side and under side—smooth. Ribs and veins—ordinary.

*Edge.*—Serrated (saw toothed).

*Serration.*—Single; small.

*Rachis.*—*Color*—Cress Green, Plate 31, on under side; upper side Brick Red, Plate 13. Under side—prickles.

*Stipules.*—Medium length; smooth.

*Disease resistance.*—Resistant.

Wood:

*New wood.*—*Color*—Rainette Green, Plate 31. *Bark*—smooth.

*Old Wood.*—*Color*—Cress Green, Plate 31. *Bark*—smooth.

Thorns (thorns are divided into thorns, prickles, and short needles):

*Thorns.*—*Quantity:* on main stalks from base—many. On laterals from stalk—ordinary. *Form*—flat base, long, hooked downward. *Color when young*—Etruscan Red, Plate 27. *Position*—irregular.

*Short needles.*—*Quantity*—on main stalks and on laterals—few.

The new variety has been asexually reproduced and the novel characteristics have been found to be established.

I claim:

A new and distinct variety of hybrid tea rose plant characterized as to novelty by its vigorous habit of growth and great floriferousness; the slender form of bud; high centered form of flower, together with the varying color combinations of its petals with associated large number of stamens when flowers are open; the long flowering stems; large number of leaflets, and the brick red color of the upper side of the leaf stems, substantially as shown and described.

VICTOR LENS.